United States Patent
Safai et al.

(10) Patent No.: US 7,287,902 B2
(45) Date of Patent: Oct. 30, 2007

(54) SYSTEMS AND METHODS FOR THERMOGRAPHIC INSPECTION OF COMPOSITE STRUCTURES

(75) Inventors: Morteza Safai, Seattle, WA (US); Gary E. Georgeson, Federal Way, WA (US); John F. Spalding, Jr., Renton, WA (US); Jeffrey G. Thompson, Kent, WA (US)

(73) Assignee: The Boeing Company, Chicago, IL (US)

( * ) Notice: Subject to any disclaimer, the term of this patent is extended or adjusted under 35 U.S.C. 154(b) by 88 days.

(21) Appl. No.: 11/146,785

(22) Filed: Jun. 7, 2005

(65) Prior Publication Data

US 2006/0274812 A1    Dec. 7, 2006

(51) Int. Cl.
*G01N 25/72* (2006.01)
(52) U.S. Cl. .............................. 374/5; 374/57; 374/121
(58) Field of Classification Search .............. 374/4–7, 374/162, 120–121, 57; 126/263
See application file for complete search history.

(56) References Cited

U.S. PATENT DOCUMENTS

| | | | |
|---|---|---|---|
| 4,327,743 A * | 5/1982 | Katz .......................... 600/549 |
| 5,035,230 A | 7/1991 | Steidl et al. |
| 5,417,494 A * | 5/1995 | Kempa et al. ................. 374/5 |
| 5,902,935 A | 5/1999 | Georgeson et al. |
| 6,004,817 A | 12/1999 | Chamberlain et al. |
| 6,220,099 B1 | 4/2001 | Marti et al. |
| 6,234,025 B1 | 5/2001 | Gieske et al. |
| 6,748,791 B1 | 6/2004 | Georgeson et al. |
| 6,843,130 B2 | 1/2005 | Georgeson |
| 6,848,312 B2 | 2/2005 | Georgeson |
| 6,945,111 B2 | 9/2005 | Georgeson |
| 2003/0041854 A1 * | 3/2003 | Sabin et al. ........... 126/263.01 |
| 2004/0065981 A1 * | 4/2004 | Grimmer et al. ........... 264/402 |
| 2004/0119020 A1 * | 6/2004 | Bodkin ....................... 250/353 |

OTHER PUBLICATIONS

C.Deemer et al, Front-flash thermal imaging characterization of continuous fiber ceramic composites, Jan. 25, 1999,7 pages.*

* cited by examiner

*Primary Examiner*—Yaritza Guadalupe-McCall
(74) *Attorney, Agent, or Firm*—Lee & Hayes, PLLC

(57) ABSTRACT

Systems and methods for thermographically inspecting a composite material or honeycombed type structures are disclosed. In one embodiment, a system includes a thermal heat source configured to be either removably coupled to or positioned proximate to the composite material to generate a localized thermal field in a selected area of the composite material. A thermal imaging device generates a visible image of the generated thermal field.

16 Claims, 5 Drawing Sheets

SYSTEMS AND METHODS FOR THERMOGRAPHIC INSPECTION OF COMPOSITE STRUCTURES

FIELD OF THE INVENTION

This invention relates generally to material inspection systems and methods and, more specifically, to systems and methods for inspecting composite materials using thermography.

BACKGROUND OF THE INVENTION

Composite materials are increasingly used as substitutes for conventional materials such as aluminum and steel alloys in various structural components due to the generally high strength-to-weight ratio inherent in composite materials. Composite materials may generally be comprised of a network of reinforcing fibers that are generally applied in layers, and a polymeric resin that substantially wets the reinforcing fibers to form an intimate contact between the resin and the reinforcing fibers.

Composite materials exhibit modes of failure that are distinct from failure modes present in conventional materials. In particular, the material may deteriorate due to mechanical fatigue and/or environmental exposure so that the various layers in the composite material debond, forming delaminated regions within the material. In addition, the material may develop cracks and or other defects. In either case, the defect may not be detected by a visual inspection of the material. Accordingly, various non-invasive methods are available that may be used to locate defects in the composite material.

For example, in one commonly used method, a surface of the composite material is lightly and repeatedly tapped with a percussive device during the inspection, and the resulting sound is noted. If the sound resulting from the surface tapping has a relatively sharp report, the area is assumed to be generally free from internal defects. Correspondingly, if the resulting sound has a relatively hollow-sounding report, an internal defect may exist within the material at the location exhibiting the characteristic report. Although the foregoing method is simple to implement, and is suitable for a field inspection of the composite material, it relies on the subjective interpretation of sounds returned from the material, and may therefore be somewhat unreliable. In another related method, a small acoustic transducer is moved across the surface of the composite material so that an acoustic signal is projected into the material. Acoustic waves that are reflected from internal structures in the composite material are then processed to determine if internal structural anomalies exist. Although the subjectivity of the inspector is removed, the method requires a relatively sophisticated apparatus that may not be available for field use.

In another known method, a surface portion of the composite material is heated using a flash discharge lamp. After a predetermined delay period, the surface portion is imaged using an infrared camera to determine if an internal defect is present. The surface temperature decay during the delay period may then be used to infer the presence of an internal defect since debonding and/or delaminations generally cause localized and identifiable changes in the thermal conductivity of the material.

The foregoing methods generally require the availability of electrical power and therefore may be difficult to use in a field environment. Other drawbacks may also preclude the use of the foregoing methods in a field environment. For example, the use of flash lamps to provide a thermal heat input to the composite panel may not be possible in certain field environments. Accordingly, there is a need in the art for systems and methods for the thermographic inspection of composite materials that avoid the foregoing limitations.

SUMMARY

The present invention comprises systems and methods for thermographically inspecting a composite material. In one aspect, a system includes a thermal heat source configured to be removably coupled to the composite material to generate a localized thermal field in a selected area of the composite material. A thermal imaging device generates a visible image of the generated thermal field.

BRIEF DESCRIPTION OF THE DRAWINGS

Embodiments of the present invention are described in detail below with reference to the following drawings.

DETAILED DESCRIPTION

The present invention relates to systems and methods for the thermographic inspection of composite materials. Many specific details of certain embodiments of the invention are set forth in the following description and in FIGS. 1 through 4 to provide a thorough understanding of such embodiments. One skilled in the art, however, will understand that the present invention may have additional embodiments, or that the present invention may be practiced without one or more of the details described in the following description. In the following discussion, it is understood that the term "composite material" refers to various composite resins, and also to composite resins that are bonded to various metals, such as aluminum, titanium, and other similar materials.

Figure 1:
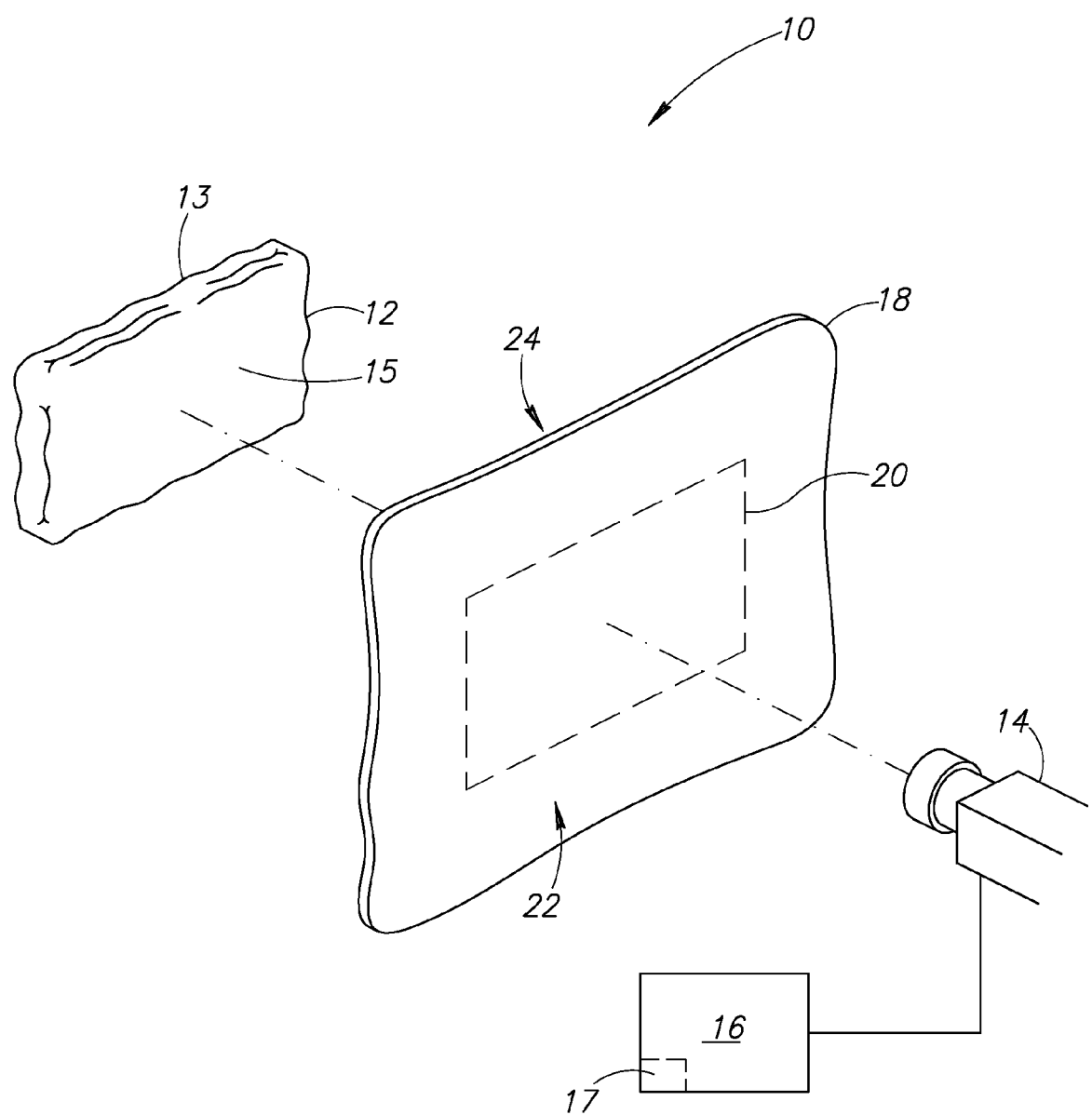
FIG. 1 is a partial isometric view of a system for thermographically inspecting a composite material, according to an embodiment of the invention.

FIG. 1 is a partial isometric view of a system 10 for thermographically inspecting a composite material, according to an embodiment of the invention. The system 10 includes a thermal heat source 12 that is operable to provide heat to a localized area of an object. Accordingly, the thermal heat source 12 may include a heat pack having a selected salt in an aqueous solution that is sealably enclosed within a container (e.g. a polymeric containment bag). In a first condition, the aqueous salt solution is maintained in a super-cooled state. In a second condition, the aqueous salt solution is activated so that an exothermic chemical reaction occurs. In one particular embodiment, for example, the exothermic chemical reaction includes a liquid-to-solid phase change (e.g. crystallization) in the solution, thus releasing the enthalpy of the phase change for the selected salt. In a selected embodiment, the selected salt includes sodium acetate. In another selected embodiment, the selected salt includes calcium nitrate tetrahydrate.

In still another embodiment, the thermal heat source 12 may include reactants that are separately maintained within the container that may be combined by rupturing an internal separator within the container that permits the reactants to be combined. In a particular embodiment, a first reactant includes an oxidizer, and a second reactant includes a liquid fuel. For example, the first reactant may include potassium permanganate, and the second reactant may include a polyol, such as ethylene glycol, as disclosed in detail in U.S. Pat. No. 5,035,230 to Steidel, et al., entitled "Disposable Food Heater", which patent is incorporated by reference. In one specific embodiment, the thermal heat source 12 includes a sodium acetate solution that is formulated to achieve a solution temperature of approximately about 125 degrees Fahrenheit, and retain this temperature for at least 35 minutes. In another specific embodiment, the thermal heat source 12 includes the foregoing potassium permanganate-polyol reactants, and may be formulated to achieve a solution temperature of approximately about 165 degrees Fahrenheit.

The thermal heat source 12 may be further configured to selectively direct the heat developed within the source 12 in a preferred direction. For example, the container (or polymeric containment bag) may have a first side 13 that includes a reflective material that substantially reduces heat transfer through the first side 13, and an opposing second side 15 that promotes heat transfer from the second side 15 and into an object by providing a conformable surface that substantially and uniformly contacts the object.

The system 10 also includes a thermal imaging device 14 that is operable to detect relatively long-wave electromagnetic radiation emitted from a selected surface area of an object, and to process the detected radiation so that a visual representation of a thermal field may be generated. Accordingly, in one specific embodiment, the thermal imaging device 14 is configured to detect electromagnetic emissions in a range between approximately about seven microns and approximately about 14 microns, and to generate a visual representation of the thermal field using a gray scale. Alternately, the visual representation of the thermal field may include a color scale. In another embodiment, the thermal imaging device 14 includes radiometric and non-radiometric infrared devices, and further includes actively cooled and uncooled full-filed thermal imaging devices. Accordingly, the thermal imaging device 14 may include the TI30 Thermal Imager, available from the Fluke Corporation of Everett, Wash., although other suitable thermal imaging devices may also be used.

The thermal imaging device 14 may also be coupled to a processor 16. The processor 16 generally includes any programmable electronic device that is configured to receive programming instructions and information, and to process the information according to the programming instructions. The processor 16 is further coupled to a plurality of external devices that are configured to perform various tasks, such as, for example, various input/output devices that permit user input commands and/or data to be transferred to the processor 16. The various input/output devices may therefore include a keyboard or keypad, a pointing device such as a mouse, or other similar data input/output devices. The processor 16 may also include a data storage device 17 to store selected information obtained from the thermal imaging device 14. Accordingly, the data storage device may include a magnetic disk storage device, or, in another particular embodiment, a solid-state memory device, such as a flash memory device, which may include an USB-compatible flash drive. In another particular embodiment, the data storage device 17 may be a removable flash media card, such as the SMART MEDIA card, available from Toshiba Corporation of Tokyo, Japan. In other particular embodiments, the data storage device may include a PCMCIA memory card, although other suitable solid-state memory devices exist.

The processor 16 may be coupled to the thermal imaging device 14 using a universal serial bus (USB) communications protocol, or by using other suitable communications protocols. For example, the processor 16 may communicate with the thermal imaging device 14 in accordance with IEEE 1394, which is commercially known as FIRE WIRE.

With reference still to FIG. 1, the operation of the system 10 will now be described in detail. The thermal heat source 12 is positioned on a selected portion of a composite material 18 so that a heat-affected zone 20 is established in the composite material 18. Accordingly, the thermal heat source 12 may be positioned on (or near) a posterior surface 24 of the composite material 18 and impressed on the surface 24 for a predetermined period of time in order to generate the heat-affected zone 20. Alternately, the thermal heat source 12 may be impressed on an anterior surface 22 of the composite material 18 to generate the heat-affected zone 20. In either case, a thermal field is generated within the heat-affected zone 20 that may be viewed using the thermal imaging device 14.

Figure 2:
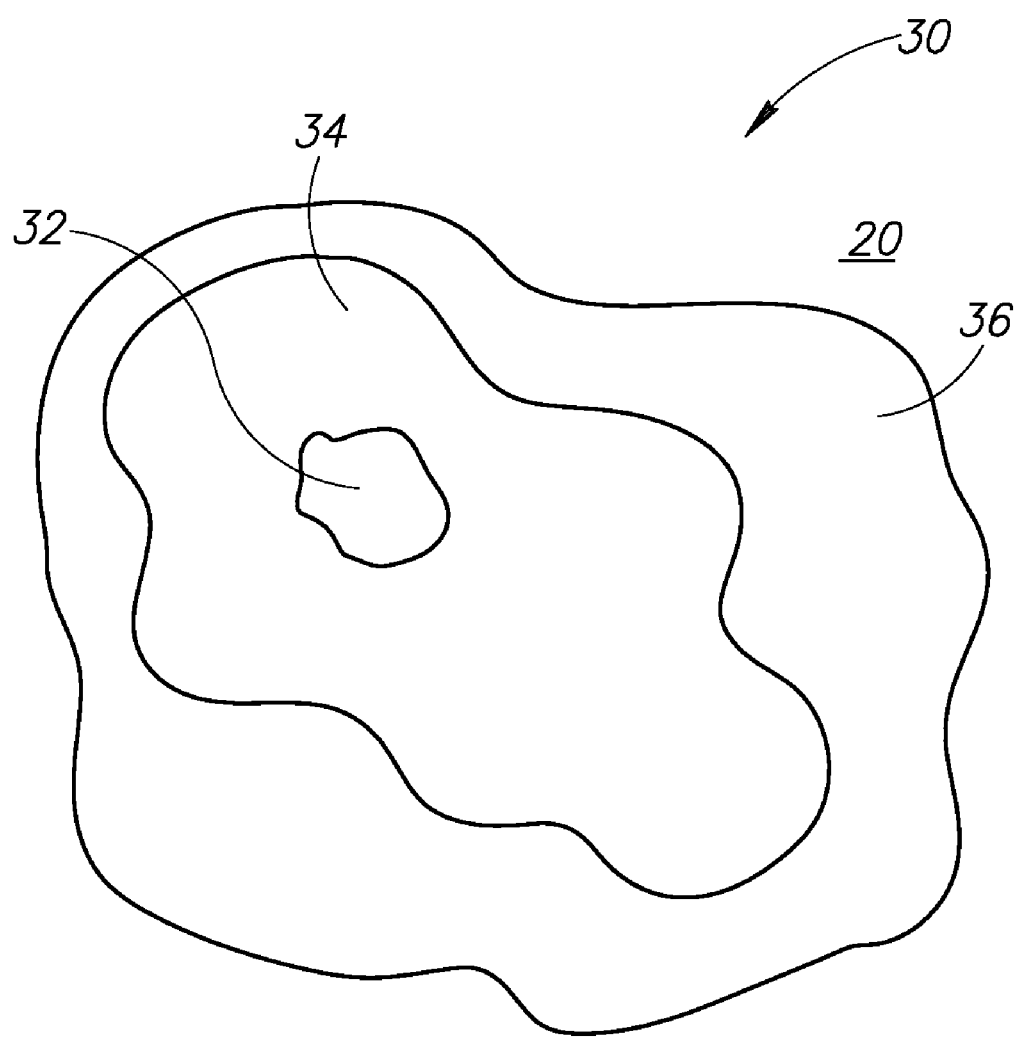
FIG. 2 is a plan view of a typical thermal field generated within the composite material undergoing a thermographic inspection.

Referring also now to FIG. 2, a plan view of a typical thermal field 30 generated within the composite material 18 is shown. As discussed briefly above, the thermal field 30 is generated within the heat-affected zone 20. If defects exist within the composite material 18, different thermal regimes are generated in the composite material 18 because the thermal conductance of the material within the heat-affected zone 20 is non-uniform. Non-uniformities in the composite material 18 may develop due to localized de-bonding of one or more layers in the composite material 18 due to an applied stress, or due to aging. Non-uniformities may also be generated within the material 18 due to a physical impact that has been absorbed by the material 18. Accordingly, due to the presence of non-uniformities within the material 18, the thermal field 30 generated in the material 18 may include a first region 32 having a first conductivity, so that the first region 32 exhibits a first color when the thermal field 30 is imaged. Similarly, a second region 34 may be present that has a second conductivity, and exhibits a second color when the thermal field 30 is imaged. A third region 36 having a third conductivity may also be present, so that a third color is viewed when the thermal field 30 is imaged. One skilled in the art will readily recognize that more than three regions, or even less that three regions may be present, depending on the particular characteristics of the non-uniformities present in the material 18.

Figure 3:
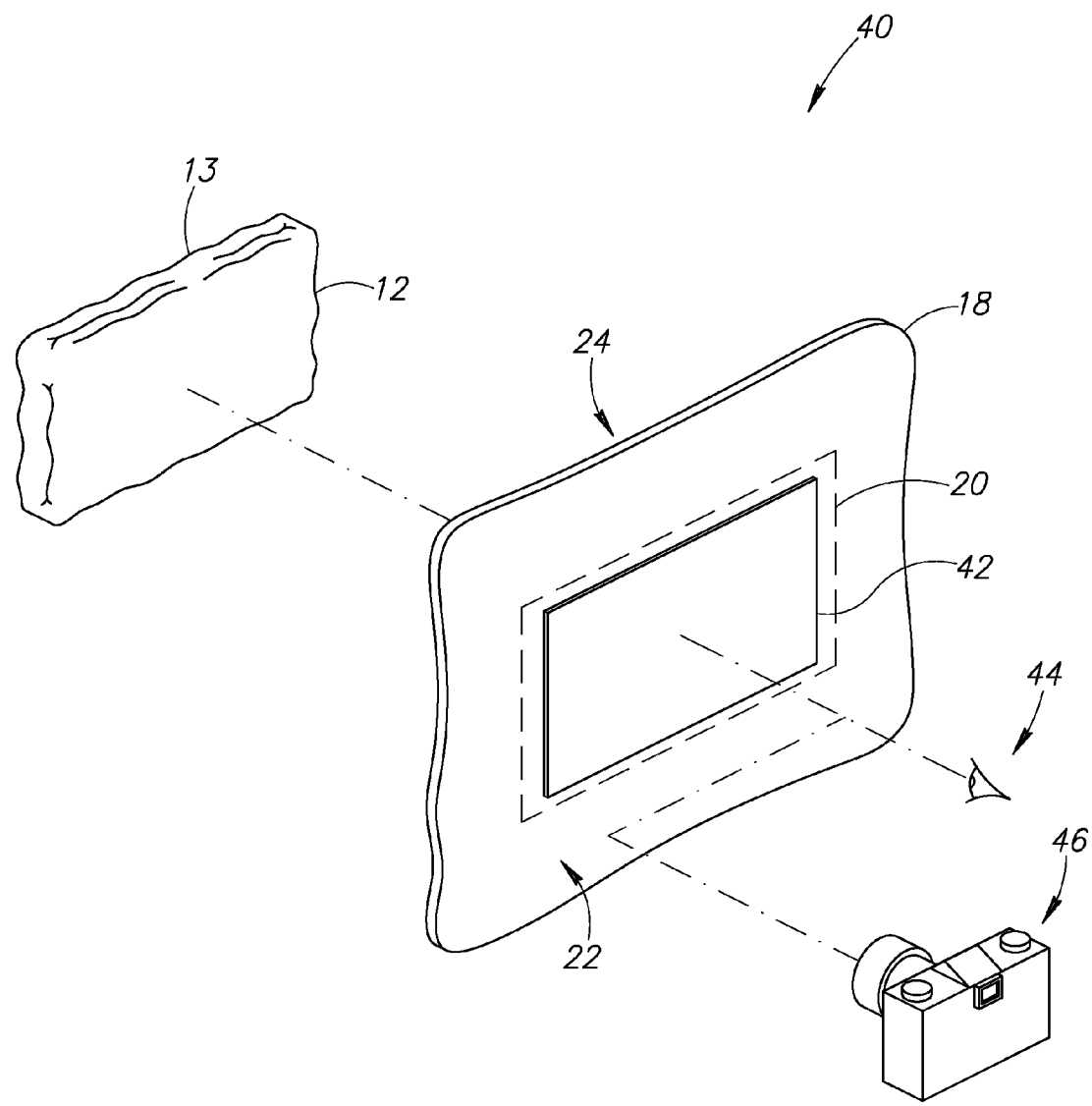
FIG. 3 is a partial isometric view of a system for thermographically inspecting a composite material, according to another embodiment of the invention.

FIG. 3 is a partial isometric view of a system 40 for thermographically inspecting a composite material, according to another embodiment of the invention. Many of the details of the present embodiment have been described in detail in connection with previous embodiments, and in the interest of brevity, will not be described further. The system 40 also includes a thermal heat source 12 that is operable to provide heat to a localized area of the composite material 18. As previously described, the thermal heat source 12 may be applied to (or positioned proximate to) an anterior surface 22 of the composite material 18, or it may be applied to the posterior surface 24. In either case, a heat-affected zone 20 is generated in the material 18 when the heat source 12 substantially contacts (or is sufficiently near) the composite material 18. For example, in various alternate embodiments, the thermal heat source 12 may be applied to one of the anterior surface 22 and the posterior surface 24 of the composite material 18 by taping the heat source 12 to the selected surface, or the heat source 12 may be provided with a self-adhering layer on a side of the heat source 12 so that upon removal of a protective layer from the self-adhering layer, the heat source 12 may be directly adhered to the selected exterior surface.

In the embodiment shown in FIG. 3, the system 40 also includes a thermographic film 42 that is applied to an exterior surface of the composite material 18. The thermographic film 42 is responsive to surface temperatures present in the heat-affected zone 20, and generates an optically viewable representation of the thermal field 30 (FIG. 2) within the heat affected zone 20. Accordingly, the thermal field 30 may be directly observed by a viewer 44. Alternately, the thermal field 30 may be recorded using a camera 46 configured to record a still or even a moving image of the thermal field 30. The camera 46 may accordingly include a digital camera, as is well known in the art, or it may include a conventional photographic camera that is configured to expose a color-sensitive film emulsion to the thermal field 30.

In one particular embodiment, the thermographic film 42 includes a thermochromic liquid crystal film. In general, a thermochromic liquid crystal may include an organic compound that may exist in a thermodynamic phase at a particular temperature that lies between the solid and liquid phases of matter. Accordingly, at a selected temperature below a predetermined event temperature, the thermochromic liquid crystal will be primarily in the solid state, and will further be relatively transparent. At a selected temperature above the event temperature, the thermochromic liquid crystal, when viewed under particular optical conditions, will reflect a unique wavelength of visible light so that a particular color may be associated with a particular temperature. In one particular embodiment, as a temperature of the thermochromic liquid crystal increases, the particular color changes from a generally red color to a generally blue color, so that a relatively continuous representation of the thermal field 30 may be generated. The thermochromic liquid crystal film may be formulated to optimize a color response in a selected temperature range, so that the film may be tailored to detect various non-uniformities that may be present in the material 18. Suitable thermochromic liquid crystal formulations are available from Hallcrest, Inc. of Glenview, Ill., although other alternative suppliers exist.

Figure 5:
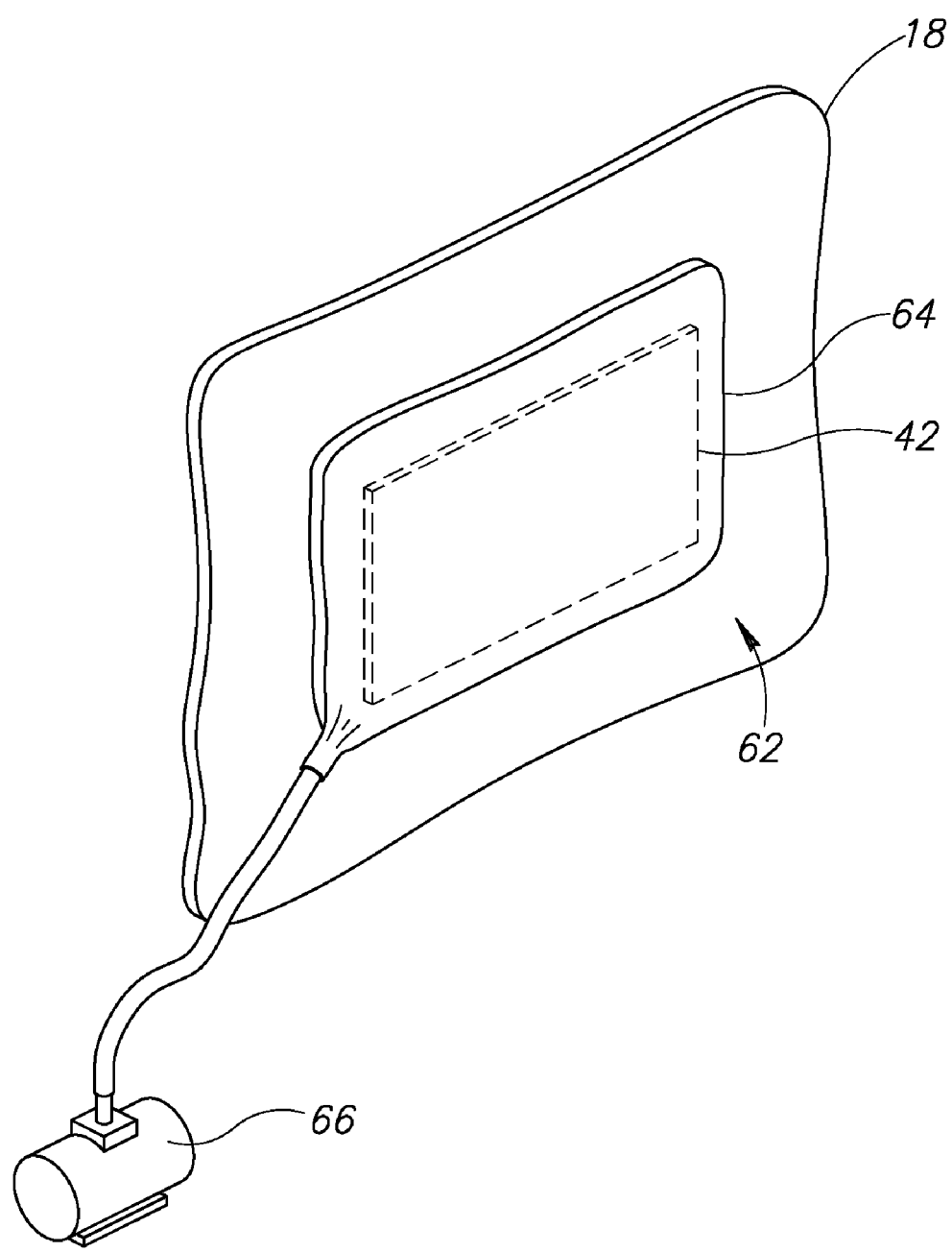
FIG. 5 is a partial isometric view of a system for thermographically inspecting a composite material, according to another embodiment of the invention.

Still referring to FIG. 3, the thermographic film 42 may be applied to an exterior surface of the material 18 using a couplant, such as an adhesive compound, a thermal grease, or even an ultrasound coupling gel. FIG. 5 is a partial isometric view of a system for thermographically inspecting a composite material, according to another embodiment. The thermographic film 42 may be applied to the exterior surface of the material 62 using a vacuum bag 64 that sealably contains the thermographic film 42. The vacuum bag 64 may be sealably attached to the exterior surface 62 and is configured to be coupled to a vacuum pump 66 that draws a vacuum relative to the ambient enviromnent within a closed interior portion of the bag. Accordingly, the thermographic film 42 may substantially contact the exterior surface 62. A suitable vacuum bag is the Model GL-1620 vacuum bag, available from Torr Technologies, Inc. of Auburn, Wash., although other suitable alternatives exist.

Figure 4:
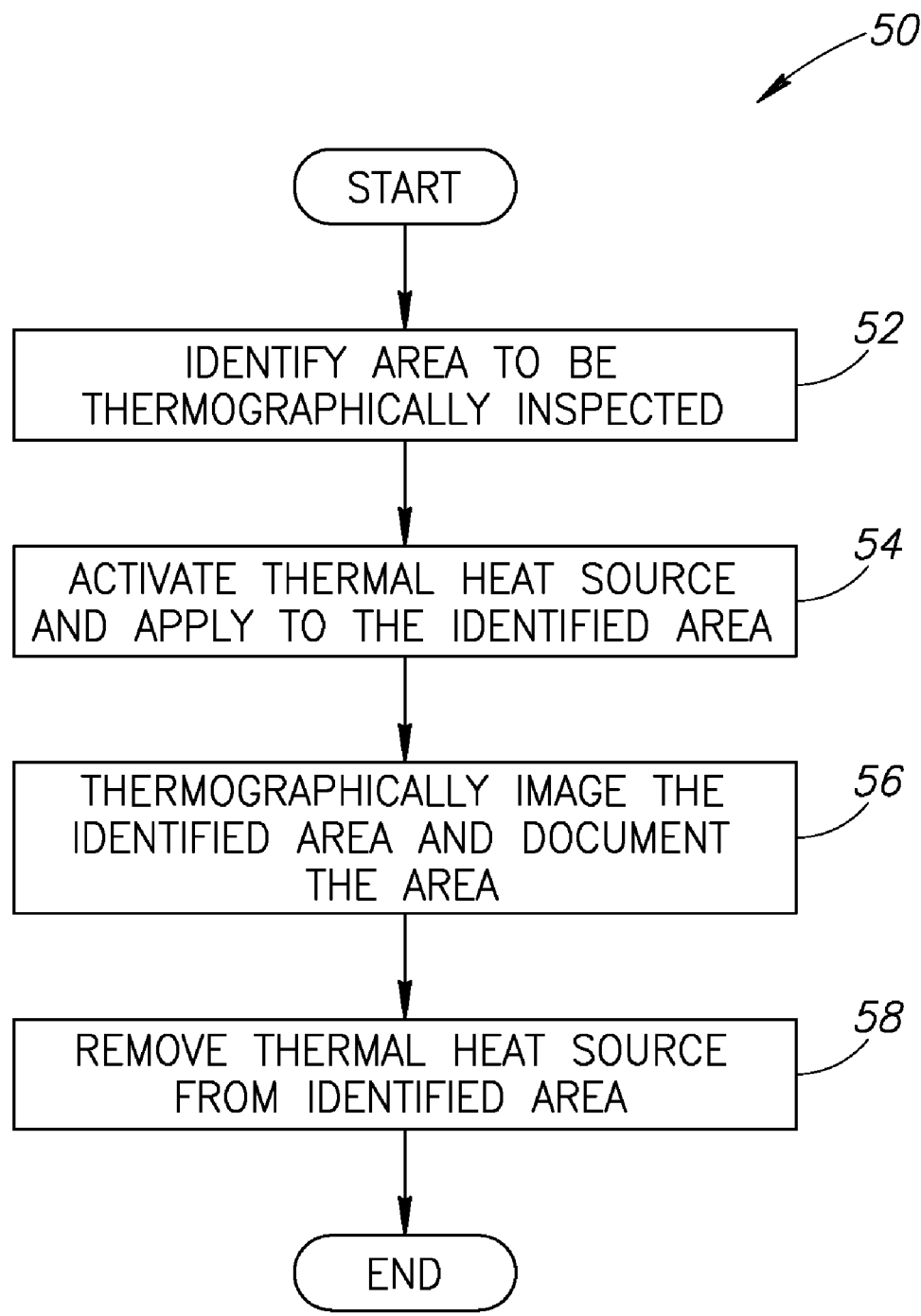
FIG. 4 is a flowchart that describes a method for thermographically inspecting a composite material, according to another embodiment of the invention.

FIG. 4 is a flowchart that will be used to describe a method 50 for thermographically inspecting a composite material, according to another embodiment of the invention. At block 52, an area that is to be thermographically inspected is identified. The identification may be based upon a direct observation of an area that has sustained physical damage. Alternately, other methods may be used to identify an area to be inspected. For example, the well-known surface-tapping test may be used to identify a damaged and/or de-bonded area in the composite material. At block 54, the thermal heat source is activated so that the affected area may be heated. In general, an activation source is located within the thermal heat source that promotes an exothermic reaction, such as an exothermic phase change (e.g. crystallization), in the solution contained within the source. Following activation of the thermal heat source, a temperature of the source escalates to a predetermined maximum temperature, and the source is brought into contact with (or near to) the identified area. The identified area may be sprayed with water, or other similar liquid materials, to improve thermal conduction between the source and the identified area. Alternately, the source may be affixed to the identified area using adhesive tape or other similar materials prior to activation of the source. In either case, the identified area is heated in order to generate the heat-affected zone. At block 56, the identified area is thermographically imaged. As discussed in greater detail in connection with previous embodiments, the identified area may be imaged using an infrared camera, or a thermographic film, such as a thermochromic liquid crystal film may be applied to the surface in order to generate a visible thermographic image. In either case, the image may be recorded as previously discussed. At block 58, the thermal heat source is removed from the identified area. Depending upon the nature of the detected damage in the composite material, a repair may be planned and performed.

Embodiments of the present invention may be included in a composite materials inspection kit that may advantageously be used in remote or "field" locations, where the availability of electrical power may be unavailable, or extremely limited. For example, the foregoing thermal heat source materials do not require electrical power for operation, and may further be restored to a super-saturated state by heating the heat source material with a cooking stove, or other similar devices. The heat affected area generated by the thermal heat source may be imaged using a thermographic film, as previously described, and the thermal response of the film may be recorded using a digital camera, or even a conventional camera that is structured to expose a color-sensitive emulsion. Alternately, a camera that is infrared-sensitive may be used to record the heat-affected area. In this case, it may not be necessary to use a thermographic film coupled to the exterior surface of the composite material.

While preferred and alternate embodiments of the invention have been illustrated and described, as noted above, many changes can be made without departing from the spirit and scope of the invention. Accordingly, the scope of the invention is not limited by the disclosure of these preferred and alternate embodiments. Instead, the invention should be determined entirely by reference to the claims that follow.

What is claimed is:

1. A system for thermographically inspecting a composite material, comprising:
    a thermal heat source configured to be at least one of engaged with and positioned proximate to the composite material to generate a localized thermal field in a selected area of the composite material; and a thermal imaging device configured to generate a visible image of the thermal field, wherein the thermal heat source comprises an aqueous solution enclosed in a container.

2. The system of claim 1, wherein the thermal heat source further comprises an aqueous solution of a selected salt that is sealably enclosed in a container.

3. The system of claim 2, wherein the selected salt comprises at least one of sodium acetate and calcium nitrate tetrahydrate.

4. The system of claim 2, wherein the selected salt is formulated to achieve a solution temperature of at least 125 degrees Fahrenheit, and to maintain the solution temperature for at least one-half hour.

5. The system of claim 1, wherein the thermal heat source further comprises a reactant group that includes an oxidizer and a liquid fuel that are separated within a containment bag until activated.

6. The system of claim 5, wherein the oxidizer comprises potassium permanganate and the fuel includes a polyol.

7. The system of claim 5, wherein the reactant group is formulated to achieve a solution temperature of at least about 165 degrees, Fahrenheit.

8. The system of claim 1, wherein the thermal heat source further comprises a first side configured to reduce heat loss from the thermal heat source, and an opposing second side configured to be applied to a surface portion of the composite material.

9. System of claim 1, wherein the thermal heat source is adapted to emit heat generated by at least one of an exothermic chemical reaction and an exothermic phase change reaction.

10. The system of claim 1, wherein the thermal imaging device further comprises at least one of an optical thermal imager configured to detect long-wave electromagnetic radiation emitted by the thermal field, and a thermographic film that is configured to be coupled to a surface portion of the composite material and responsive to surface temperatures in the thermal field.

11. The system of claim 10, wherein the thermal imaging device comprises a thermographic film having a thermochromic liquid crystal film that is formulated to respond to the surface temperatures.

12. The system of claim 11, further comprising a thermal couplant interposed between the thermochromic liquid crystal film and the surface portion of the composite material.

13. The system of claim 11, wherein the thermochromic liquid crystal film further comprises a vacuum bag that may be evacuated to impress the liquid crystal film against the surface portion of the composite material.

14. A thermographic imaging kit for field inspecting a composite material, comprising:

a thermal heat source configured to transmit heat to the composite material to generate a localized thermal field in a selected area of the composite material following an activation of the source; and a thermal imaging device configured to generate a visible image of the thermal field;

wherein the thermal heat source comprises at least one of an aqueous solution of a selected salt that is sealably enclosed in a containment bag, and a reactant group that includes an oxidizer and a liquid fuel that are separated within a containment bag until activated.

15. The thermographic imaging kit of claim 14, wherein thermal imaging device further comprises at least one of an infrared camera and a thermochromic liquid crystal film configured to be applied to a surface of the composite material.

16. The thermographic imaging kit of claim 14, further comprising a camera configured to record electromagnetic radiation at visible wavelengths, and a processor coupled to the infrared camera that is operable to process thermal data acquired by the infrared camera and to store the processed data in a memory device.

* * * * *